United States Patent [19]
Baldwin

[11] Patent Number: 6,007,572
[45] Date of Patent: Dec. 28, 1999

[54] THERMAL SEAT AND METHOD FOR USING A THERMAL SEAT

[75] Inventor: Wayne D. Baldwin, Asheboro, N.C.

[73] Assignee: Vesture Corporation, Asheboro, N.C.

[21] Appl. No.: 09/069,730

[22] Filed: Apr. 30, 1998

[51] Int. Cl.⁶ ........................................... A61F 7/00
[52] U.S. Cl. ............................................. 607/114; 297/380
[58] Field of Search ........................... 607/108, 112, 607/114; 297/380, 180.11, 183.5

[56] References Cited

U.S. PATENT DOCUMENTS

| | | |
|---|---|---|
| D. 343,088 | 1/1994 | Owens . |
| D. 346,062 | 4/1994 | Owens . |
| 3,879,598 | 4/1975 | Darling . |
| 4,060,276 | 11/1977 | Lindsay . |
| 4,258,706 | 3/1981 | Shank . |
| 4,413,857 | 11/1983 | Hayashi . |
| 4,650,245 | 3/1987 | Nazar . |
| 5,190,350 | 3/1993 | Hwang et al. ........................... 297/380 |
| 5,205,610 | 4/1993 | Reninger ................................ 297/380 |
| 5,300,105 | 4/1994 | Owens . |
| 5,339,541 | 8/1994 | Owens . |
| 5,357,693 | 10/1994 | Owens . |
| 5,500,010 | 3/1996 | Owens . |
| 5,516,193 | 5/1996 | Simpson ................................ 297/252 |
| 5,545,198 | 8/1996 | Owens . |
| 5,575,812 | 11/1996 | Owens . |
| 5,591,221 | 1/1997 | Owens . |
| 5,601,744 | 2/1997 | Baldwin . |
| 5,630,959 | 5/1997 | Owens . |
| 5,700,284 | 12/1997 | Owens . |
| 5,727,844 | 3/1998 | O'Quinn et al. . |
| 5,785,427 | 7/1998 | Godshaw .................................. 383/4 |

Primary Examiner—Linda O. M. Dvorak
Assistant Examiner—Roy Gibson
Attorney, Agent, or Firm—Merchant & Gould P.C.

[57] ABSTRACT

A thermal seat is provided including a seat panel and a back panel. The seat panel includes a first rigid support, a second rigid support, and a cushioned region. Similarly, the back panel includes a first rigid support, a second rigid support, and a central cushioned region. The thermal seat additionally includes first and second straps attaching the seat panel and the back panel to provide a predetermined angle between the seat panel and the back panel. The interaction between these components of the thermal seat provide for a sturdy and comfortable sitting arrangement. The thermal seat additionally includes a thermal unit constructed for being received within the central cushioned region of the seat panel or the back panel. Alternatively, the thermal unit can be provided in both the seat panel and the back panel. A method for using the thermal seat is provided by altering the temperature of the thermal unit, and introducing the thermal unit into either the seat panel or the back panel.

10 Claims, 2 Drawing Sheets

THERMAL SEAT AND METHOD FOR USING A THERMAL SEAT

FIELD OF THE INVENTION

The invention relates to a thermal seat having support member and to a method of using a thermal seat having support member.

BACKGROUND OF THE INVENTION

Thermally heated seats are disclosed in several prior patents. For example, see U.S. Pat. Nos. 5,545,198; 5,700,284; 5,300,105; 5,357,693; and D343,088, all of which are assigned to Vesture Corporation, the assignee of the above-identified application. These patents generally describe seat cushions which include a removable envelope enclosing a fluid which can be heated in a microwave oven.

It is well known that liquid-containing heating pads are designed to heat parts of the human body to help heal injuries, alleviate soreness, and provide comfort in cold environments. Heating pads may be conventional hot water bottles, which can be filled with heated liquid, or may be modern, sealed liquid pouches, which can be heated by microwave energy. In recent years, heating pads of flexible plastic envelopes containing water-based solutions have been manufactured and sold. Such pads are manufactured by placing them in a vacuum pump and evacuating the air within the envelopes. The envelopes are then heat sealed with the liquid therein. Certain microwavable heating pads tend to retain heat for up to several hours, depending on their design.

Portable seat cushions are popular accessories for concert spectators, sports fans, campers, fisherman, and outdoor enthusiasts in general. Heating pads have been installed inside seat cushions to keep spectators and the like warm when using the seat cushions in cold conditions. A seat cushion having a removable heating pad for easy heating in a microwave oven is described in U.S. Pat. No. 5,545,198 to Owens. Certain other prior art seat cushions include heating pads which often do not remain in the centers of the cushions, which is where the heating pads function most effectively. A comfortable back rest is also often lacking in certain prior art seat cushions.

SUMMARY OF THE INVENTION

A thermal seat is provided by the present invention. The thermal seat includes a seat panel and a back panel. The seat panel includes a first rigid support, a second rigid support, and a cushioned region. Similarly, the back panel includes a first rigid support, a second rigid support, and a central cushioned region. The thermal seat additionally includes first and second straps attaching the seat panel and the back panel to provide a predetermined angle between the seat panel and the back panel. The interaction between these components of the thermal seat provide for a sturdy and comfortable sitting arrangement. The thermal seat additionally includes a thermal unit constructed for being received within the central cushioned region of the seat panel or the back panel. Alternatively, the thermal unit can be provided in both the seat panel and the back panel.

A method for using the thermal seat is provided by the invention. The method includes providing a thermal seat as described above, altering the temperature of the thermal unit, and introducing the thermal unit into either the seat panel or the back panel. The temperature of the thermal unit can be altered by heating in a microwave oven or cooling in a refrigerator or freezer.

DETAILED DESCRIPTION OF THE PREFERRED EMBODIMENT

Figure 1:
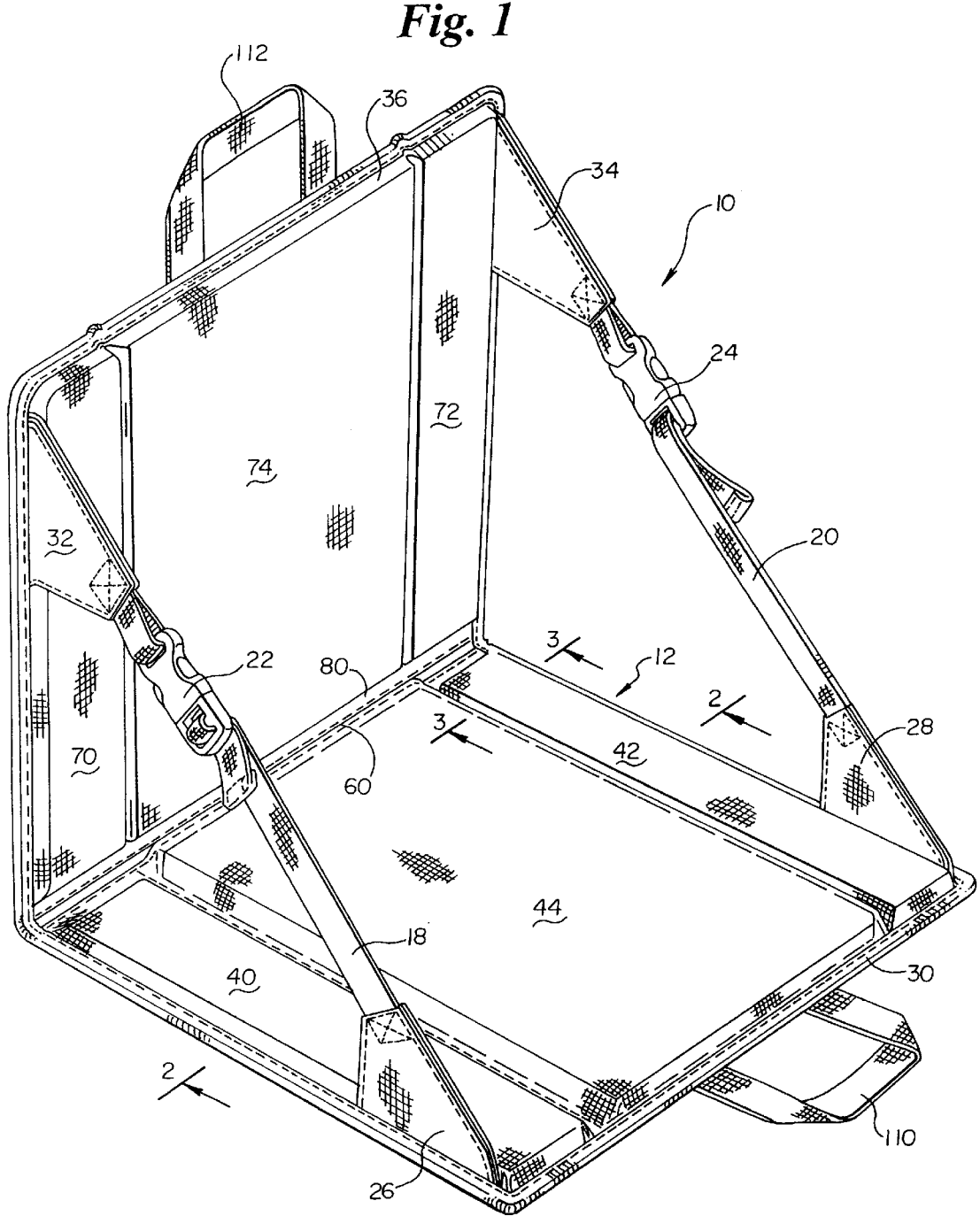
FIG. 1 is a perspective view of the thermal seat according to the principles of the present invention in an open position.
Figure 2:
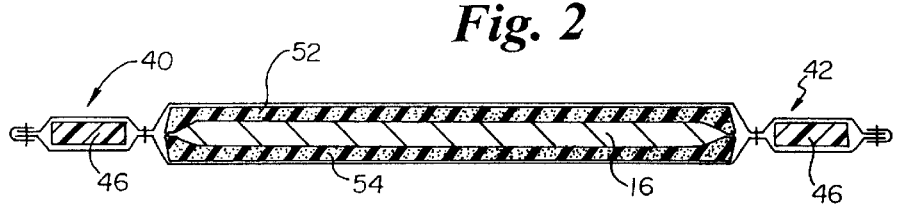
FIG. 2 is a sectional view of the thermal seat shown in FIG. 1 taken along line 2—2.
Figure 3:
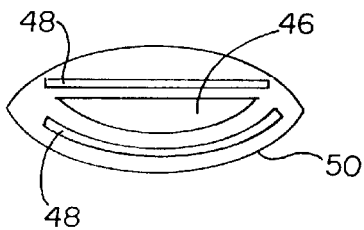
FIG. 3 is a sectional view of the support member of the thermal seat of FIG. 1 taken along line 3—3.

Now referring to FIGS. 1–4, a preferred embodiment of the thermal seat according to the invention is provided at reference 10. The use of the term "thermal" is intended to reflect that the thermal seat 10 can be either heated or cooled and provide the individual using the seat with sustained warming or cooling over a period of time. For example, the thermal seat 10 can provide the user with heat when used in a relatively cold environment, or it can absorb heat from the user when provided in a relatively hot environment.

The thermal seat 10 includes a seat panel 12 and a back panel 14. The seat panel 12 includes a thermal unit 16. The thermal unit 16 is removable from the thermal seat 10 and can be either heated in a microwave oven or cooled in a refrigerator or freezer. It should be appreciated that while the invention is described with respect to a thermal seat 10 having a thermal unit 16 in the seat panel 12, the thermal unit 16 can be provided in the back panel 14, or two thermal retention units can be provided wherein one is provided in the seat panel 12 and the other is provided in the back panel 14. It is an advantage of the present invention that the seat panel 12 and the back panel 14 can be provided as essentially identical structures. That is, both can be constructed so they are capable of receiving the thermal unit 16.

The thermal seat 10 is shown in FIG. 1 in an open, sitting position. The seat panel 12 and the back panel 14 can be restrained from fully opening by the presence of the side straps 18 and 20. As shown, these side straps 18 and 20 are adjustable so that the angle between the seat panel 12 and the back panel 14 can be adjusted for comfort. In preferred applications, the angle between the seat panel 12 and the back panel 14 can be adjusted between about 45° F. and about 120° F. when provided in an open, sitting position. The side straps 18 and 20 include buckles 22 and 24. When the buckle 22 and 24 are disconnected, the back panel 14 can be reclined so that the angle between the seat panel 12 and the back panel 14 can be provided with essentially any desirable angle. It is expected that when the buckles 22 and 24 are released, the angle between the seat panel 12 and the back panel 14 will be about 180° so that the thermal seat can be laid flat as a resting mat.

The side straps 18 and 20 are connected to the seat panel 12 by side supports 26 and 28. The side supports 26 and 28 are preferably provided near the forward edge 30 of the seat panel 12 to provide increased support. The side straps 18 and 20 are connected to the back panel 14 by the side supports 32 and 34 which are provided near the upward edge 36 of the back panel 14.

The seat panel 12 includes three general regions. These regions include a first rigid side support region 40, a second rigid side support region 42, and a central cushioned region 44. The first rigid side region 40 includes a rigid member 46 surrounded by foam layers 48 and enclosed within an envelope 50. The envelope 50 is then inserted along the length of the first rigid side region 40. The second rigid side region 42 includes a rigid member 46 surrounded by foam layers 48 and enclosed within an envelope 50 which is then inserted along the length of the second rigid side 42. It should be appreciated that the regions are separated by seams so that the components within each region stay contained.

The central cushion region 44 includes a first foam member 52 and a second foam member 54. Provided between the first and second foam members 52 and 54 is the thermal unit 16. The seat panel 12 includes an interior edge 60 provided with a hook and loop fastening element along its length. The hook and loop fastening element allows access into the central cushion region 44. Accordingly, the thermal unit 16 can be removed from the central cushion region 44 and reintroduced therein after it has been subjected to heating or cooling.

The back panel 14 similarly includes three general regions. These regions include a first rigid side support region 70, a second rigid side support region 72, and a central cushioned region 74. The first rigid side region 70 includes a rigid member 46 inserted along the length of the first rigid side region 70. The second rigid side region 72 includes a rigid member 46 inserted along the length of the second rigid side region 72. It should be appreciated that a preferred rigid member includes rattan because of its structural integrity and lightness. Of course, other types of rigid members could similarly be used. The central cushioning region 74 includes a first foam member and a second foam member similar to the seat panel 12. A thermal unit can be provided between the first foam member and the second foam member. The back panel 14 includes an interior edge 80 provided with a hook and loop fastening element along its length. The hook and loop fastening element allows access into the central cushioned region 74. This allows removal and reintroduction of a thermal unit into the central cushioned region 74. It should be appreciated that in a preferred embodiment of the invention, only the seat panel 12 includes the thermal unit 16. Of course, the thermal unit 16 can be included only in the back panel 14, or thermal unit 16 can be provided in both the seat panel 12 and the back panel 14.

The thermal element 16 includes a flexible envelope 90 and a material 92 therein which can be heated by microwave energy or cooled by placement in a refrigerator or freezer. A preferred thermal unit which can be used in the invention is described by U.S. Pat. No. 5,545,198 to Owens, the entire disclosure of which is incorporated herein by reference. In particular, the thermal unit is described by U.S. Pat. No. 5,545,198 at column 5, line 12 through column 6, line 4, the specific disclosure of which is incorporated herein by reference. This type of thermal unit is available from Vesture Corporation under the mark Microcore®. It should be appreciated that various other types of thermal units can be used provided that they are flexible and are capable of being heated in a microwave oven or cooled in a refrigerator or freezer. It is generally preferred, however, that the thermal unit be one which resists leakage even if punctured. The fluid within the thermal unit can be water or other types of aqueous slurry, including water with adjuvant such as preservative.

Figure 4:
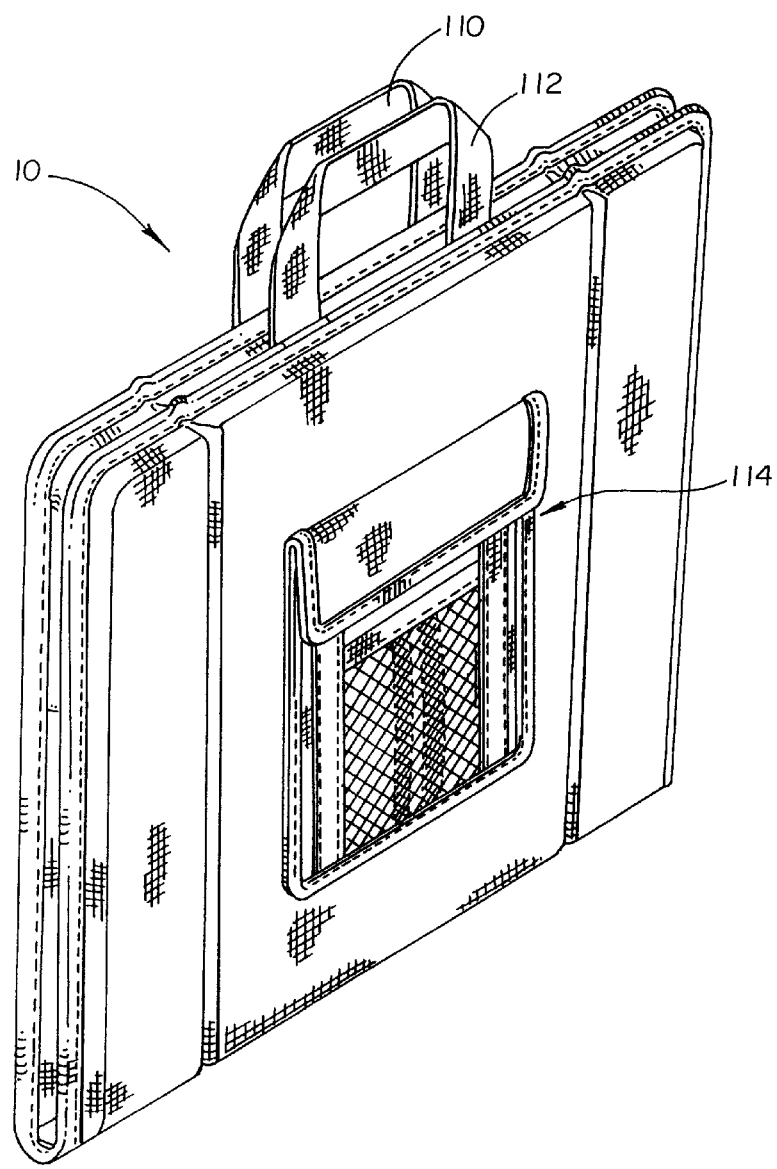
FIG. 4 is a perspective view of the thermal seat according to the principles of the present invention in a closed position.

Now referring to FIG. 4, the thermal seat 10 is provided in a closed position. The thermal seat 10 includes carrying straps 110 and 112 and a pocket 114 for storage of accessories such as gloves, tissue, etc.

I claim:

1. A thermal seat comprising:

a seat panel including a first rigid support, a second rigid support, and a central cushioned region comprising a first foam member and a second foam member;

a back panel including a first rigid support, a second rigid support, and a central cushioned region;

first and second straps attaching the seat panel and the back panel to provide a predetermined angle between the seat panel and the back panel; and a thermal unit constructed for being received within the central cushioned region of the seat panel between the first foam member and the second foam member, wherein the thermal unit can be introduced into the central cushioned region and removed from the central cushioned region through an opening in the central cushioned region provided along an interior edge of said seat panel adjacent said back panel.

2. A thermal seat according to claim 6, further comprising handles for carrying the thermal seat.

3. A thermal seat according to claim 1, wherein the central cushioned region of said back panel comprises a first foam member and a second foam member.

4. A thermal seat according to claim 3, wherein said back panel includes an interior edge adjacent said seat panel for inserting and removing said thermal unit from within the first foam member and the second foam member of the central cushioned region of said back panel.

5. A method for using a thermal seat having support member, the method comprising steps of:

(a) providing a thermal seat comprising:
      a seat panel including a first rigid support, a second rigid support, and a central cushioned region comprising a first foam member and a second foam member;
      a back panel including a first rigid support, a second rigid support, and a central cushioned region;
      first and second straps attaching the seat panel and the back panel to provide a predetermined angle between the seat panel and the back panel; and
      a thermal unit constructed for being received within the central cushioned region of the seat panel between the first foam member and the second foam member, wherein the thermal unit can be introduced into the central cushioned region and removed from the central cushioned region through an opening in the central cushioned region provided along an interior edge of said seat panel adjacent said back panel;

(b) altering the temperature of the thermal unit; and (c) placing the thermal unit within the central cushioned region of said seat panel.

6. A method according to claim 5, wherein said step of altering the temperature of the thermal unit comprises heating the thermal unit in a microwave oven.

7. A method according to claim 5, wherein said step of altering the temperature of the thermal unit comprises cooling the thermal unit in a freezer.

8. A method according to claim 5, wherein the central cushioned region of said back panel comprises a first foam member and a second foam member.

9. A method according to claim 5, wherein said back panel includes an interior edge adjacent said seat panel for inserting and removing said thermal unit from within the first foam member and the second foam member of the central cushioned region of said back panel.

10. A method according to claim 9, comprising placing a thermal unit within the central cushioned region of said back panel.

* * * * *